United States Patent [19]

Hardtmann

[11] 3,931,183
[45] *Jan. 6, 1976

[54] 1-SUBSTITUTED-2-DISUBSTITUTEDAMINO-PYRIDO[2,3-D]PYRIMIDIN-4(1H)-ONES

[75] Inventor: Goetz E. Hardtmann, Florham Park, N.J.

[73] Assignee: Sandoz Inc., E. Hanover, N.J.

[ * ] Notice: The portion of the term of this patent subsequent to Jan. 6, 1993, has been disclaimed.

[22] Filed: July 24, 1974

[21] Appl. No.: 491,249

Related U.S. Application Data

[63] Continuation-in-part of Ser. No. 437,471, Jan. 28, 1974, abandoned.

[52] U.S. Cl. .................. 260/256.4 F; 260/247.7 K; 260/293.85; 424/250
[51] Int. Cl.² .................................. C07D 239/00
[58] Field of Search ..................... 260/256.4 F

[56] References Cited
UNITED STATES PATENTS 3,794,637  2/1974  Wiedemann et al. ........ 260/256.4 F Primary Examiner—Donald G. Daus
Assistant Examiner—James H. Turnipseed
Attorney, Agent, or Firm—Gerald D. Sharkin; Richard E. Vila

[57] ABSTRACT

Anti-histaminics of the formula

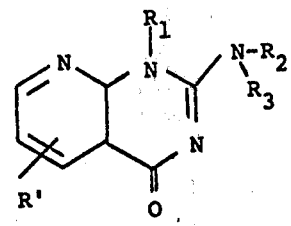

wherein $R_1$ is alkyl, alkenyl or phenalkyl, $R_2$ and $R_3$ are alkyl or alkenyl and $R'$ is optional are prepared by alkylating or alkenylating a 1-substituted-2-monosubstituted-amino pyrido 2,3-d pyrimidin-4(1H)-one with an alkyl halide or alkenyl halide.

10 Claims, No Drawings

1-SUBSTITUTED-2-DISUBSTITUTEDAMINO-PYRIDO[2,3-D]PYRIMIDIN-4(1H)-ONES

This application is a continuation-in-part of copending application Ser. No. 437,471, filed Jan. 28, 1974, now all abandoned.

This invention relates to 1,2-disubstituted-pyrido[2,3-d]pyrimidin-4(1H)-ones, their preparation and the compositions and methods utilizing the pharmacological activity of said compounds.

The compounds of the invention may be represented by the structural formula I:

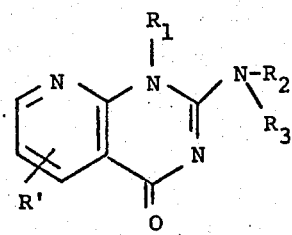

wherein
$R_1$ is alkyl of 1 to 6 carbon atoms, alkenyl of 3 to 8 carbon atoms or phenalkyl of the formula II:

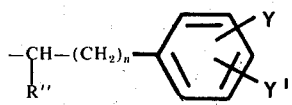

$n$ is 0 or 1

$R''$ is hydrogen or methyl, preferably with $R''$ being hydrogen when $n$ is 1

$R_2$ and $R_3$ are independently alkyl of 1 to 4 carbon atoms or alkenyl of 3 to 6 carbon atoms, preferably at least one of which is straight chain, and more preferably both $R_2$ and $R_3$ are straight chain, $R'$ is hydrogen or alkyl of 1 to 3 carbon atoms, and Y and Y' are independently hydrogen, halo of atomic weight of from 18 to 36, alkyl of 1 to 3 carbon atoms or alkoxy of 1 to 3 carbon atoms or one is hydrogen and the other bromo or trifluoromethyl.

The compounds of the formula I may be prepared in a Step A reaction by reacting a compound of the formula II:

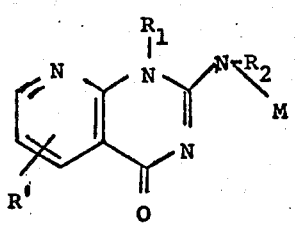

in which $R'$, $R_1$ and $R_2$ are as defined and M is hydrogen or an alkali metal, preferably sodium, with a compound of the formula III:

in which $R_3$ is as defined and X is halo of atomic weight of from 35 to 127, preferably iodo or bromo.

The reaction of Step A is of known type and preferably effected employing a compound II in which M is an alkali metal. Such compounds II may be prepared from the corresponding compound II in which M is hydrogen in a known manner involving the reaction of a compound II in which M is hydrogen with a strong base such as an alkali metal hydride or alkoxide, preferably sodium hydride. The reaction is conveniently effected at from 0°C. to 50°C., preferably at about room temperature, in an inert solvent which can be employed as solvent for the reaction of Step A. The conversion of the metallo substituted pyrido[2,3-d]pyrimidinone of the formula II to the desired product of the formula I may be carried out at temperatures of from 0°C. to 100°C., preferably 10°C. to 40°C. and conveniently at room temperature. When the Step A reaction is carried out with a compound II in which M is hydrogen, the reaction is conducted in the presence of the strong base, e.g. sodium hydride. The reaction generally is conducted on the basis that it may also lead to the formation of a by-product in which the 3-position of the compound of the formula II is alkylated or alkenylated. However, the desired product of the formula I may be isolated from the reaction mixture of Step A and separated from such byproduct by working up by conventional procedures.

The compounds of the formula II may be prepared in a Step B by reacting a compound of the formula IV:

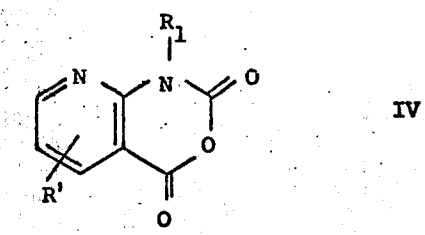

wherein $R_1$ and $R'$ are as above defined, with a compound of the formula V:

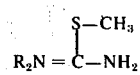

wherein $R_2$ is as defined.

The preparation of compounds II by the reaction of Step B can be carried out at temperatures in the range of 20°C. to 200°C., more usually 80°C. to 180°C., preferably 100°C. to 180°C. The reaction is conveniently carried out in an organic solvent of conventional type providing an inert reaction medium. The higher boiling solvent for use at reflux temperatures represent the preferred solvents, e.g.. toluene, xylene and especially diglyme and the like. The reaction is preferably carried out in the presence of a base, e.g., potassium hydroxide, sodium hydroxide, barium hydroxide and potassium carbonate; and when the compound V is employed directly in acid addition salt form, it is of course desirable to employ an amount of base greater than the amount necessary to neutralize the acid. It will be appreciated by those skilled in the art that the compounds of the formula V are tautomeric and have the alternative and equivalent structure represented by the formula VA:

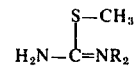

wherein $R_2$ is as defined.

The compounds of the formulae IV and V are either known or may be produced from known materials by established procedures.

The compounds of the formula I of the invention are useful because they possess biological activity. In particular, the compounds of the formula I are useful as agents for relieving the symptomatic effects of the release of histamine, i.e., as anti-histaminic agents, as indicated by observing the respiratory status on oral administration (1.0–100 mgs./kgs.) to the unanesthetized guinea pig exposed to aerosolized histamine dihydrochloride according to a modification of the method of Van Arman et al. J. Pharmacol. Exptl. Therap. 133: 90–97, 1961. For such use and depending upon known variables satisfactory results are obtained in general on the daily administration of from 0.5 to 100 milligrams per kilogram of body weight, preferably given in divided doses to 2 to 4 times a day, or in sustained release form. For most mammals the administration of from 40 to 1600 milligrams per day provides satisfactory results and dosage forms suitable for internal administration comprise 10 to 800 milligrams of the compound in admixture with a solid or liquid pharmaceutical carrier or diluent.

The preferred compounds of the invention from the standpoint of anti-histaminic activity are those in which $R_1$ is benzyl including substituted benzyl, particularly unsubstituted benzyl and halobenzyl, e.g. fluorobenzyl, especially 4-halobenzyl, and the more preferred compounds are those in which R' is hydrogen.

For the use indicated above, the compounds may be combined with a pharmaceutically acceptable carrier, and such other conventional adjuvants as may be necessary, and administered orally or parenterally. For most uses oral administration with carriers is preferred and may take place in such conventional forms as tablets, dispersible powders, granules, capsules, suspensions, syrups and elixirs. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g., calcium carbonate, calcium phosphate and kaolin. The preferred pharmaceutical compositions from the standpoint of preparation and ease of oral administration are solid compositions, particularly hard-filled capsules and tablets. Parenteral administration may be in such conventional forms as injectionable solutions and suspensions.

A representative formulation is a tablet for oral administration 2 to 4 times a day for relieving the effect of histamine release and prepared by conventional tabletting techniques to contain the following ingredients:

| Ingredients | Weight (mg.) |
| --- | --- |
| 1-(4'-fluorobenzyl)-2-dimethyl-amino-pyrido[2,3-d]pyrimidin-4(1H)-one | 10 |
| Tragacanth | 10 |
| Lactose | 222.5 |
| Corn Starch | 25 |
| Talcum | 15 |
| Magnesium Stearate | 2.5 |

The following examples show representative compounds encompassed within the scope of this invention and the manner in which such compounds are prepared. However, it is to be understood that the examples are for purposes of illustration only.

EXAMPLE A 1-(4'-fluorobenzyl)-2-methylamino-pyrido[2,3-d]pyrimidin-4(1H)-one.

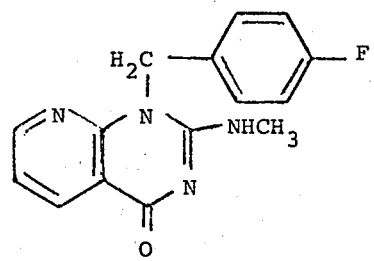

A mixture of 25 g. of 4-(4'-fluorobenzyl)-3,4-dihydro-1,3-dioxo-1H-pyrido[2,3-d][1,3]oxazine, 15 g. of S,N-dimethylthiopseudourea (hydrogen iodide), 15 g. of anhydrous potassium carbonate and 300 ml. of diglyme is refluxed with stirring for 4 hours. The resulting mixture is filtered while hot through Celite and the precipitate formed on cooling is recovered by filtering, washed with diglyme and then three times with ether and then dried under reduced pressure. The resulting product is dissolved in methylene chloride/methanol, filtered to remove insoluble material, concentrated on a steam bath and treated with ether to crystallize the titled product (free base form), m.p. 242°–246°C.

EXAMPLE 1

1-(4'-fluorobenzyl)-2-dimethylamino-pyrido[2,3-d]pyrimidin-4(1H)-one.

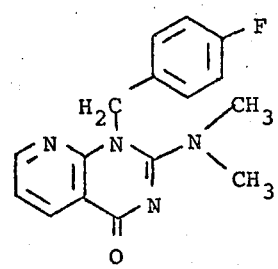

To a suspension of 10.0 g. of powdered 1-(4'-fluorobenzyl)-2-methylamino-pyrido[2,3-d]pyrimidin-4(1H)-one in 300 ml. of tetrahydrofuran is added portionwise over the course of 5 minutes 4.8 g. of potassium t-butoxide and the resulting mixture is stirred at room temperature for 45 minutes. There is then added 6.5 g. of methyl iodide followed by stirring at room temperature for two days. The resulting mixture is filtered through celite and the filtrate evaporated to dryness. The residue is dissolved in 100 ml. of methylene chloride, washed twice with water, dried, filtered and evaporated to dryness. The residue is dissolved in a small amount of chloroform and filtered through a 650 ml. filter column using silica and chloroform. The combined product containing fractions are evaporated to dryness, the residue dissolved in 50 ml. of methylene chloride and ether added while warming on a steam bath to obtain 1-(4'-fluorobenzyl)-2-dimethylamino-pyrido[2,3-d]pyrimidin-4(1H)-one, m.p. 167°–170°C.

EXAMPLE 2

Following the procedure of Example 1, the following additional compounds of the invention are prepared:

A) 1-benzyl-2-dimethylamino-pyrido[2,3-d]pyrimidin-4(1H)-one.
B) 1-ethyl-2-dimethylamino-pyrido[2,3-d]pyrimidin-4-(1H)-one.
C) 1-(4'-fluorobenzyl)-2-diethylamino-pyrido[2,3-d]pyrimidin-4(1H)-one.
D) 1-(4'-chlorobenzyl)-2-dimethylamino-pyrido[2,3-d]pyrimidin-4(1H)-one.
E) 1-(3',4'-dimethoxybenzyl)-2-dimethylamino-pyrido[2,3-d]pyrimidin-4(1H)-one.
F) 1-(4'-fluorobenzyl)-2-N-methyl-N-allylamino-pyrido[2,3-d]pyrimidin-4(1H)-one.
G) 1-(4'-(bromobenzyl)-2-dimethylamino-pyrido[2,3-d]pyrimidin-4(1H)-one.
H) 1-(4'-fluorobenzyl)-7-methyl-2-dimethylamino-pyrido[2,3-d]pyrimidin-4c1H)-one.
I) 1-allyl-2-dimethylamino-pyrido[2,3-d]pyrimidin-4(1H)-one.

The compounds of the formula VI, defined above, may also be prepared in a Step C reaction involving cyclizing a compound of the formula VI:

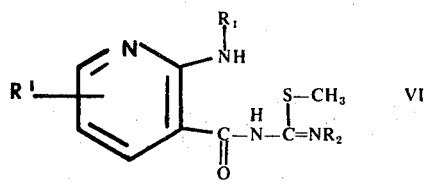

wherein R', $R_1$ and $R_2$ are as defined.

The preparation of compounds of the formula II by the reaction of Step C may be carried out by heating a compound of the formula VI at elevated temperatures preferably in the range of 120°C. to 200°C., more preferably 130°C. to 180°C. and desirably in the presence of an inert solvent and strong base. The inert solvents may be of conventional type and are preferably the higher boiling solvents, e.g., diglyme. Suitable strong bases include the strong inorganic bases such as the alkali metal hydroxides, e.g., sodium hydroxide. Reaction time may vary, particularly with temperature, with good results usually obtain in one-half to ten hours.

The compounds of the formula VI employed in Step C may be prepared by reacting a compound of the formula IV with a compound of the formula V under controlled temperature and time conditions. In general, temperatures are usually in the range of from 20°C. to 120°C., preferably 60°C. to 115°C. Reaction times may be typically of the order of from 10 minutes to 5 hours and generally will vary inversely with reaction temperature. The reaction is preferably carried out in the presence of a base such as an inorganic base, e.g., potassium carbonate and sodium carbonate, and in the presence of an inert solvent of conventional type. The solvents boiling at reflux temperatures are generally preferred, e.g., acetonitrile, benzene and toluene. The resulting product of the formula VII may, if desired, be isolated and recovered by working up by conventional procedures.

It will be evident that the compounds of the formula VI exist in and be expressed by the alternative and equivalent tautomeric form having the formula VIA:

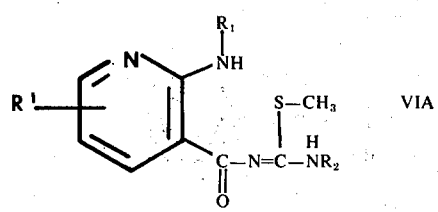

in which R, $R_1$ and $R_2$ are as defined.

EXAMPLE B 1-(4'-fluorobenzyl)-2-allylamino-pyrido[2,3-d]pyrimidin-4(1H)-one

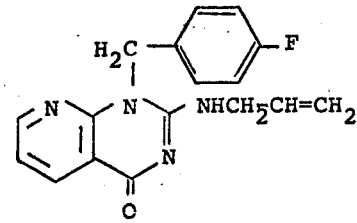

A mixture of 27 g. of 4-(4'-fluorobenzyl)-3,4-dihydro-1,3-dioxo-1H-pyrido[2,3-d] [1,3]oxazine, 27.5 g. of S-methyl-N-allylthiopseudourea (hydrogen iodide), 12 g. of anhydrous sodium carbonate and 250 ml. of acetonitrile is refluxed with stirring for one hour. The resulting mixture is evaporated to dryness, the residue dissolved in methylene chloride, filtered through celite and the filtrate evaporated in vacuo. The resulting oil is dissolved in 150 ml. of diglyme and refluxed for 1.5 hours. The resulting reaction mixture is cooled and the resulting crystalline material is recovered by filtering, washed with diglyme and then twice with ether, dried in a high vacuum, dissolved in methylene chloride/methanol, filtered, concentrated on a steam bath and ether added to obtain 1-(4'-fluorobenzyl)-2- allylamino-pyrido [2,3-d]pyrimidin-4(1H)-one, m.p. 190°–194°C.

EXAMPLE 3

Following the procedure of Example 1, the following additional compound of the invention is prepared:

A) 1-(4'-fluorobenzyl)-2-diallylamino-pyrido[2,3-d]pyrimidin-4(1H)-one.

What is claimed is:

1. A compound of the formula

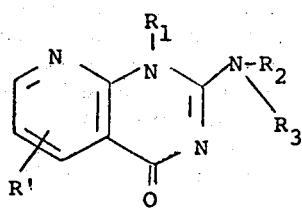

wherein $R_1$ is alkyl of 1 to 6 carbon atoms, alkenyl of 3 to 8 carbon atoms or phenalkyl of the formula:

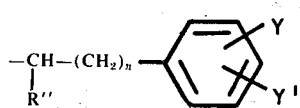

$n$ is 0 to 1

R'' is hydrogen or methyl, $R_2$ and $R_3$ are independently alkyl of 1 to 4 carbon atoms or alkenyl of 3 to 6 carbon atoms, R' is hydrogen or alkyl of 1 to 3 carbon atoms, and Y and Y'' are independently hydrogen, fluoro, chloro, alkyl of 1 to 3 carbon atoms or alkoxy of 1 to 3 carbon atoms or one is hydrogen and the other bromo or trifluoromethyl.

2. A compound of claim 1 in which $R_1$ is alkyl.
3. A compound of claim 2 in which R' is hydrogen.
4. A compound of claim 1 in which each of $R_2$ and $R_3$ is alkyl.
5. A compound of claim 1 in which $R_1$ is

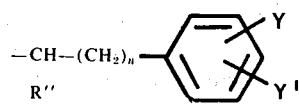

6. A compound of claim 5 in which R'' is hydrogen, $n$ is 0, Y is hydrogen, fluoro, chloro or bromo and Y' is hydrogen, fluoro or chloro, with the proviso that Y' is hydrogen when Y is bromo.
7. A compound of claim 6 in which R' is hydrogen.
8. A compound of claim 5 in which each of $R_2$ and $R_3$ is alkyl.
9. A compound of claim 7 in which each of $R_2$ and $R_3$ is methyl.
10. The compound of claim 9 which is 1-(4'-fluorobenzyl)-2-dimethylamino-pyrido[2,3-d]pyrimidin-4(1H)-one.

* * * * *